Feb. 25, 1936. W. SPANDIKOW, JR Plant Pat. 167
ROSE
Filed Oct. 23, 1935
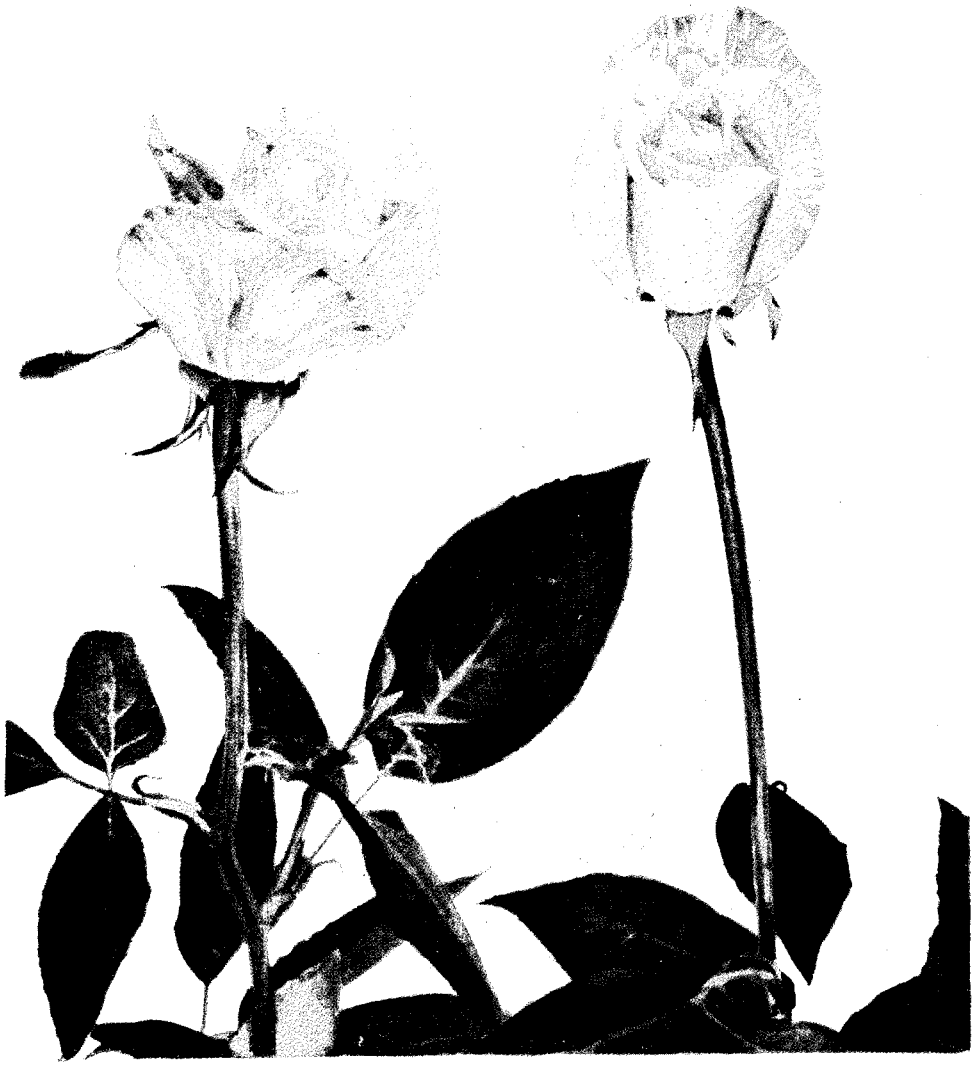
Inventor
William Spandikow, Jr
by Rummler Rummler & Woodworth
attys.

Patented Feb. 25, 1936

Plant Pat. 167

UNITED STATES PATENT OFFICE

167

ROSE

William Spandikow, Jr., Maywood, Ill., assignor to William Spandikow & Sons, Maywood, Ill., a copartnership composed of William Spandikow, Sr., William Spandikow, Jr., and Elmer A. Spandikow Application October 23, 1935, Serial No. 46,366

1 Claim. (Cl. 47—61)

This discovery relates to a sport of the Briarcliff rose and is a new and distinct variety of hybrid tea rose. The bloom of the new rose is decidedly novel in its markings, and possesses highly productive and other desirable qualities which will be hereinafter described.

The base color of this new rose is "Rose Madder" (Alizarin) (Winsor & Newton Color Specimens) irregularly splotched and striped radially from the base of the petals with "Madder Lake" and "Pink Madder" (Winsor & Newton Color Specimens), varying in size from mere dots to sometimes one-third the area of the petals.

The accompanying illustration shows in full color two average specimen blooms of the new rose, illustrating the unusual markings of the petals as well as the long, stiff and practically thornless erect stems.

This rose was discovered growing as a sport on a Briarcliff rose bush and has been asexually propagated by budding and its distinctive characteristics are now thoroughly established and fixed.

In comparison with its parent plant, the well-known Briarcliff rose, my new rose is of much stronger growth; it is far more prolific in production of bloom—a conservative estimate being from 18 to 22 blooms a year from each plant. It is practically thornless, there being oftentimes but one short and weak thorn on a stem, has more luxuriant foliage, and the leaves are longer and narrower, and duller green in tone.

Other characteristics of this new rose, in its habit of growth, which makes it outstanding from the Briarcliff or any of the Briarcliff sports, are the absence of blind or dormant eyes below the place where cuttings are usually made; its bloom does not discolor; its resistance to disease and the persistence of its petals in hanging on until they dry, which feature makes this rose an excellent shipper in its ability to withstand a great deal of abuse in handling.

The following is a more detailed description of this new rose plant and flower:

Parentage:
- Sport.
- *Parent variety.*—Briarcliff.
- *Classification.*—Hybrid tea.

*Flower*

Blooming habit:
- *Recurrent.*—Continuous.

Bud:
- *Size.*—Large.
- *Form.*—Pointed. Not affected by wet or hot weather.
- *Color.*—Shows evidence of the novel markings as soon as sepals first divide and these progress with development of bud.
- *Sepals.*—Serrated—curl back when bud half open.
- *Calyx.*—Pear-shaped; small; smooth and without special odor when rubbed.
- *Peduncle.*—Length, medium; aspect, smooth; color, medium green; stiff, erect and heavy.
- *Opening.*—Opens well and is not affected by adverse conditions.

Bloom:
- *Size.*—Large; average size when fully expanded, 3½ to 4 inches.
- *Borne.*—Singly.
- *Stems.*—Long, strong.
- *Form.*—High center.
- *Permanence.*—Retains its form to the end.
- *Petalage.*—Normally from 22 to 25.

Color:
- Entire flower is "Rose Madder" (Alizarin) (Winsor & Newton Color Specimens) irregularly splotched and striped with "Madder Lake" and "Pink Madder" (Winsor & Newton Color Specimens) which is the same on the inside and reverse of petals. Does not discolor.

Petals:
- *Texture.*—Thick, unaffected by wet or hot weather.
- *Appearance.*—Inside and outside, shiny.
- *Form.*—Notched and pointed.
- *Arrangement.*—Regular.

Petaloids:
- Few.
- *Persistence.*—Hang on and dry.
- *Fragrance.*—Moderate tea.
- *Lasting quality.*—On the plant and as a cut flower, very long.

Sexual organs:
- *Stamens, Anthers.*—Small, white.
- *Pollen.*—Lemon yellow.
- *Styles.*—Bunched, even, short and medium.

*Stigmas.*—White in color.
*Ovaries.*—Some protruding from calyx.

Fruit:
Fertile.
*Form.*—Round, seeds protruding.
*Aspect.*—Smooth.
*Color at maturity.*—Black.
*Sepals.*—Permanent.

*Plant*

Form:
Bush.

Growth:
Very vigorous, upright, compact.

Foliage:
3 or 5 leaflets.
*Size.*—Medium.
*Quantity.*—Normal.
*Color.*—New foliage—upper side—normal green; under side, light green.
*Old foliage.*—Upper side, dark green; under side, light green.
*Shape.*—Oval pointed.
*Texture.*—Upper side—leathery; under side, smooth.
*Ribs and veins.*—Prominent.
*Edge.*—Serrated.
*Leaf stem.*—Green; underside, smooth.
*Disease resistance.*—Resistant.

Wood:
*New wood.*—Color, reddish; bark, smooth.
*Old wood.*—Color, green; bark, smooth.

Thorns:
*Quantity.*—On main stems and laterals, very few and weak.
*Color when young.*—Transparent.
*Position.*—Irregular.
*Prickles.*—On main stalks and laterals—few. Color—green.
*Short needles.*—Quantity—none on main stalks and laterals.

The main distinguishing characteristics of my new rose, either separately or in combination, are as follows:

1. Unusual markings of the bloom.
2. Flower stems are remarkably smooth, being free from spines, and almost entirely free from thorns which are small and weak.
3. Tenaciousness of the petals, both on the plant and as a cut flower, making it very desirable, especially as an excellent shipper.
4. Its vigor, superior keeping qualities, ease of propagation and freedom from disease.
5. Rapid renewal of new growth, and the absence of blind or dormant eyes below where cuttings are usually made.

Having thus described my invention, I claim:

A variety of rose as disclosed, characterized by the new and novel markings of its bloom of "Rose Madder" (Alizarin) and splotched and striped radially from the base of each petal with "Madder Lake" and "Pink Madder", long, stiff and practically thornless stems, superior shipping qualities, its vigor and resistance to disease.

WILLIAM SPANDIKOW, JR.